United States Patent
Hara et al.

(10) Patent No.: US 9,737,467 B2
(45) Date of Patent: Aug. 22, 2017

(54) BODY ODOR SUPPRESSING AGENT

(71) Applicant: MANDOM CORPORATION, Osaka, Osaka (JP)

(72) Inventors: Takeshi Hara, Osaka (JP); Hironori Shimizu, Osaka (JP)

(73) Assignee: MANDOM CORPORATION, Osaka (JP)

( * ) Notice: Subject to any disclaimer, the term of this patent is extended or adjusted under 35 U.S.C. 154(b) by 0 days.

(21) Appl. No.: 15/346,698

(22) Filed: Nov. 8, 2016

(65) Prior Publication Data

US 2017/0049672 A1 Feb. 23, 2017

Related U.S. Application Data

(63) Continuation of application No. 14/415,493, filed as application No. PCT/JP2013/082619 on Dec. 4, 2013, now abandoned.

(30) Foreign Application Priority Data

Dec. 7, 2012 (JP) .................................. 2012-268359

(51) Int. Cl.
  *A61K 8/29* (2006.01)
  *A61K 8/02* (2006.01)
  *A61K 8/04* (2006.01)
  *A61K 8/19* (2006.01)
  *A61Q 15/00* (2006.01)

(52) U.S. Cl.
  CPC .............. *A61K 8/29* (2013.01); *A61K 8/0241* (2013.01); *A61K 8/0279* (2013.01); *A61K 8/046* (2013.01); *A61K 8/19* (2013.01); *A61Q 15/00* (2013.01); *A61K 2800/412* (2013.01); *A61K 2800/621* (2013.01); *A61K 2800/651* (2013.01)

(58) Field of Classification Search
  None
  See application file for complete search history.

(56) References Cited

U.S. PATENT DOCUMENTS

| 5,965,479 A | 10/1999 | Suzuki et al. |
| 2002/0110689 A1 | 8/2002 | Hu et al. |
| 2003/0100445 A1 | 5/2003 | Ueda et al. |
| 2007/0017453 A1 | 1/2007 | Fritter et al. |
| 2008/0194447 A1 | 8/2008 | Oki |
| 2012/0258853 A1 | 10/2012 | Veeraraghavan et al. |

FOREIGN PATENT DOCUMENTS

| CN | 101090742 A | 12/2007 |
| EP | 0 411 206 A1 | 2/1991 |
| JP | 2-224761 A | 9/1990 |
| JP | 4-256436 A | 9/1992 |
| JP | 8-208211 A | 8/1996 |
| JP | 9-234364 A | 9/1997 |
| JP | 2002-145747 A | 5/2002 |
| JP | 2005-263610 A | 9/2005 |
| JP | 2009-209043 A | 9/2009 |
| JP | 2011-148785 A | 8/2011 |
| JP | 2014-516903 A | 7/2014 |
| WO | WO-2006/071318 A1 | 7/2006 |

OTHER PUBLICATIONS

International Search Report for the Application No. PCT/JP2013/082619 mailed Mar. 4, 2014.
(Edited by) Mitsui, Takeo, "New Cosmetic Science (Shin Keshouhingaku)", Nanzando Co., Ltd., 2001, second edition, pp. 510-515.
Wu, Jufang, "Modeling adsorption of organic compounds on activated carbon" 2004, printed in Sweden, pp. 1-74 (see p. 7).
Qingdao Guan Baolin Activated Carbon Co., Ltd. ([obtained from on-line website http://www.qdgbl.com/EN/index.asp, last visit May 5, 2016]).
Supplementary European Search Report for the Application No. EP 13 86 1351 dated May 12, 2016.
Written Opinion of the International Searching Authority (PCT/ISA/237) for Application No. PCT/JP2013/082619 mailed Mar. 4, 2014.

*Primary Examiner* — Ernst V Arnold
*Assistant Examiner* — Kyung Sook Chang
(74) *Attorney, Agent, or Firm* — Cheng Law Group, PLLC

(57) ABSTRACT

The present invention provides a body odor suppressing agent that contains activated carbon and that has excellent body odor suppressing effects, causes no black soiling on an object to be coated, and has excellent practical aptitude. The present invention also provides a body odor suppressing agent having an excellent feeling of use when the agent is applied to the skin. The present invention further provides a body odor suppressing agent capable of preventing nozzles from clogging when the agent is packed into a spray container and used. The body odor suppressing agent of the present invention includes a titanium oxide-coated activated carbon including an activated carbon having an average particle diameter of 15 to 50 μm and a titanium oxide present over the surface of the activated carbon.

4 Claims, No Drawings

BODY ODOR SUPPRESSING AGENT

CROSS-REFERENCE TO RELATED APPLICATIONS

This application is a Continuation Application of patent application Ser. No. 14/415,493, filed on Jan. 16, 2015, which is a 371 application of Application Serial No. PCT/JP2013/082619, filed on Dec. 4, 2013, which is based on Japanese Patent Application No. 2012-268359 filed on Dec. 7, 2012, the entire contents of which are hereby incorporated by reference.

TECHNICAL FIELD

The present invention relates to a body odor suppressing agent. Specifically, the present invention relates to a body odor suppressing agent that is applied to skin to exert excellent deodorizing effects on body odor such as hircismus.

BACKGROUND ART

Hircismus, foot odor, sweat odor, and other body odors, which make people uncomfortable, are typically generated by decomposition of a mixture of sweat and lipids such as sebum by skin normal florae. For example, hircismus results from, for example, the odor of fatty acids as degradation products of lipids contained in secretions secreted from the apocrine glands present on the axilla.

In order to suppress such body odor, various techniques such as bactericides, antiperspirants, and deodorants have been used (for example, see Non-Patent Document 1). For example, deodorant; compositions containing zinc oxide and silica as deodorant components are known (for example, see Patent Document 1 and Patent Document 2), However, much higher suppressive function on the body odor has been demanded. For example, a deodorant component having more excellent deodorizing function has been demanded.

A skin lotion for removing body odor has been developed while focusing on the adsorption function of charcoal. The skin lotion is prepared by mixing a common skin lotion with coconut shell activated carbon and other components (see Patent. Document 3).

CITATION LIST

Patent Literature

Patent Document 1: JP-A No, 2011-148785
Patent Document 2: JP-A No. 2009-209043
Patent Document 3: JP-A No. 2002-145747

Non-Patent Literature

Non-Patent Document 1: "New Cosmetic Science (Shin Keshouhingaku)", second edition, edited by Takeo Mitsui. NANZANDO Co., Ltd., pp. 510-515 (2001)

SUMMARY OF INVENTION

Technical Problem

The inventors of the present invention have found that activated carbon has excellent a deodorizing function as compared with conventional deodorant components such as zinc oxide and have attempted to prepare a body odor suppressing agent containing activated carbon. However, when the body odor suppressing agent containing activated carbon is applied to the skin, clothes, or the like by spraying or other means, the skin or the like coated with the body odor suppressing agent is soiled with black residue, and this attempt reveals that such an agent is unsuited for practical use In addition, when applied to the skin, the agent causes roughness on the skin after coating, and has a lower feeling of use. Moreover, when packed into a spray container and used, the agent readily causes clogging of the nozzle. Patent Document 3 describes no problem of the soiling, the feeling of use, or the clogging of nozzles at all. In other words, no body odor suppressing agent containing activated carbon, but causing no black soiling on an object to be coated, such as the skin, and having excellent practical aptitude has been found, as well no body odor suppressing agent having an excellent feeling of use or no body odor suppressing agent capable of preventing nozzles from clogging has also been found.

Therefore, it is an object of the present invention to provide a body odor suppressing agent that contains activated carbon and that has excellent body odor suppressing effects, causes no black soiling on an object to be coated, and has excellent practical aptitude. An object of the present invention is to provide a body odor suppressing agent having an excellent feeling of use when the agent is applied to the skin. An object of the present invention is to provide a body odor suppressing agent capable of preventing nozzles from clogging when the agent is packed into a spray container and used.

Solution to Problem

As a result of intensive studies, the inventors of the present invention have found that by mixing a titanium oxide-coated activated carbon in which a titanium oxide is present over the surface of an activated carbon having an average particle diameter within a particular range, a body odor suppressing agent having excellent body odor suppressing effects, causing no black soiling on an object to be coated, such as the skin, and having excellent practical aptitude can be obtained, have found that the body odor suppressing agent also has an excellent feeling of use when the agent is applied to the skin and that the agent can prevent nozzles from clogging when the agent is packed into a spray container and used, and have accomplished the present invention.

In other words, the present invention provides a body odor suppressing agent including a titanium oxide-coated activated carbon including an activated carbon having an average particle diameter of 15 to 50 μm and a titanium oxide present over a surface of the activated carbon.

The titanium oxide preferably has an average particle diameter of 0.01 to 0.5 μm.

The titanium oxide preferably has a weight ratio of 500 to 1,500 parts by weight relative to 100 parts by weight of the activated carbon.

Advantageous Effects of Invention

A body odor suppressing agent of the present invention has the configuration above and thus has excellent body odor suppressing effects. The body odor suppressing agent causes no black soiling on an object to be coated, such as the skin when applied to the skin, clothes, or the like by spraying or other means and has excellent practical aptitude. When the body odor suppressing agent is applied to the skin, the skin after coating is smooth, and the agent has an excellent feeling of use. In addition, when packed into a spray container and used, the body odor suppressing agent can prevent nozzles from clogging.

DESCRIPTION OF EMBODIMENTS

A body odor suppressing agent of the present invention includes a titanium oxide-coated activated carbon as an essential component. The titanium oxide-coated activated carbon is a complex having the configuration in which a titanium oxide is present over the surface of activated carbon. The titanium oxide-coated activated carbon used may be one type or two or more types.

In the present specification, the titanium oxide-coated activated carbon in the body odor suppressing agent of the present invention is also called "titanium oxide-coated activated carbon (A)". The activated carbon constituting the titanium oxide-coated activated carbon (A) is also called "activated carbon (a)" The titanium oxide constituting the titanium oxide-coated activated carbon (A) is also called "titanium oxide (b)".

In other words, the titanium oxide-coated activated carbon (A) at least contains an activated carbon (a) and a titanium oxide (b) present over the surface of the activated carbon (a). The titanium oxide-coated activated carbon (A) may contain other components in addition to the activated carbon (a) and the titanium oxide (b). Each of the activated carbon (a), the titanium oxide (b), and the other components except the activated carbon (a) and the titanium oxide (b) may be one type or two or more types.

The activated carbon (a) is not particularly limited but is a porous carbonaceous material. The activated carbon (a) may contain hydrogen, oxygen, inorganic components, and other components in addition to carbon. The activated carbon (a) is not particularly limited but is preferably a powdered activated carbon.

The activated carbon (a) may be prepared from any raw material, which can be a raw material commonly used for activated carbon. Specific examples of the raw material include coconut shell, wood, sawdust, coal, phenol resins, rayon, acrylonitrile, coal pitch, and petroleum pitch. Among them, coconut shell, wood, phenol resins, and coal are preferred.

The activated carbon (a) has an average particle diameter (average particle size) of 15 to 50 μm, preferably 18 to 45 μm, and more preferably 20 to 42 μm. An activated carbon (a) having an average particle diameter within the range allows the titanium oxide-coated activated carbon (A) to be white. The body odor suppressing agent of the present invention thus causes no black soiling (hereinafter also called "application soiling") on an object to be coated, such as the skin, when applied, and also has excellent body odor suppressing effects. The body odor suppressing agent has an excellent feeling of use when applied to the skin. The body odor suppressing agent of the present invention can prevent nozzles from clogging when packed into a spray container and used. If the average particle diameter is less than 15 μm, the titanium oxide-coated activated carbon becomes gray to black (the color tones of the titanium oxide-coated activated carbon change to a range of gray to black) and thus readily causes application soiling. If a large amount of a titanium oxide is applied to make the titanium oxide-coated activated carbon white, the adsorption capacity is deteriorated. Such a titanium oxide-coated activated carbon thus fails to satisfy both the prevention of application soiling and the body odor suppressing effects. If containing an activated carbon having an average particle diameter of more than 50 μm, the body odor suppressing agent causes roughness and has a lower feeling of use when applied to the skin. Such an agent is likely to cause clogging of nozzles when packed into a spray container and used.

The "average particle diameter of the activated carbon (a)" means an average particle diameter of the whole activated carbon constituting the titanium oxide-coated activated carbon (A). In the present specification, the average particle diameter of the activated carbon (a) can be determined by a laser diffraction scattering method with a laser diffraction scattering particle size analyzer "MT3300" (manufactured by NIKKISO CO., LTD.) or other analyzers.

The central pore size of the activated carbon (a) is not particularly limited, but is preferably 0.1 to 10 nm and more preferably 0.5 to 2.0 nm in terms of improving the adsorption capacity of the titanium oxide-coated activated carbon to improve the body odor suppressing effects. The central pore size of the activated carbon (a) can be determined, for example, by the BET method with a pore size distribution analyzer "Belsorp" (manufactured by BEL Japan, Inc.) or other analyzers.

The iodine adsorption number of the activated carbon (a) is not particularly limited, but is preferably 100 to 3,000 mg/g and more preferably 500 to 2,000 mg/g in terms of improving the adsorption capacity of the titanium oxide-coated activated carbon to improve the body odor suppressing effects. In the present specification, the iodine adsorption number of the activated carbon (a) can be determined by the titrimetry (JIS K 1417).

The activated carbon (a) can be produced by a known production method. For example, the activated carbon (a) can be produced by pulverizing and classifying a known activated carbon. The activated carbon (a) may be commercial products. Examples of the commercial product include, but are not necessarily limited to, trade name "Taiko A" (manufactured by FUTAMURA CHEMICAL CO., LTD.).

The titanium oxide (b) is not particularly limited and can be a known titanium oxide (titanium dioxide). Examples of the titanium oxide (b) include, but are not necessarily limited to, rutile-type titanium oxides, anatase-type titanium oxides, and brookite-type titanium oxides.

The average particle diameter of the titanium oxide (b) is not particularly limited, but is preferably 0.001 to 1.0 μm, more preferably 0.01 to 0.5 μm, even more preferably 0.1 to 0.4 μm, and further more preferably 0.2 to 0.3 μm. A titanium oxide (b) having an average particle diameter within the range improves the effect of making the titanium oxide-coated activated carbon (A) white to improve the effect of preventing application soiling of the body odor suppressing agent of the present invention, and thus is preferred. If the average particle diameter is less than 0.001 μm, the titanium oxide-coated activated carbon (A) becomes gray to black. Such a body odor suppressing agent may cause application soiling and have lower practical aptitude.

The "average particle diameter of the titanium oxide (b)" means an average particle diameter of the whole titanium oxide constituting the titanium oxide-coated activated carbon (A). In the present specification, the average particle diameter (sphere equivalent diameter) of the titanium oxide (b) can be calculated from a specific surface area determined by the BET method (or a simple BET method).

The titanium oxide (b) may be commercial products. Examples of the commercial product include, but are not necessarily limited to, trade name "Tipaque CR-50" (manufactured by ISHIHARA SANGYO KAISHA, LTD.) and trade name "MT-700B" (manufactured by Tayca Corporation).

The titanium oxide-coated activated carbon (A) may contain resins. The resin is used as a binder resin, for example. Examples of the resin include, but are not necessarily limited to, polyester resins, acrylic resins, urethane resins, vinyl acetate resins, ethylene-vinyl acetate resins, epoxy resins, silicone resins, polystyrene resins, and cellulose resins. Among them, acrylic resins (specifically aqueous acrylic resins) are preferred and are exemplified by alkyl acrylate copolymers.

The titanium oxide-coated activated carbon (A) may contain metal salts, for example.

In the titanium oxide-coated activated carbon (A), the weight ratio of the titanium oxide (b) relative to 100 parts by weight of the activated, carbon (a) is not particularly limited, but is preferably 10 to 10,000 parts by weight, more preferably 100 to 5,000 parts by weight, even more preferably 500 to 2,000 parts by weight, further more preferably 500 to 1,500 parts by weight, still more preferably 550 to 1,050 parts by weight, and most preferably 600 to 1,000 parts by weight. In other words, the ratio of [activated carbon (a): titanium oxide (b)] (weight ratio) is preferably 1:0.1 to 1:100, more preferably 1:1 to 1:50, even more preferably 1:5 to 1:20, further more preferably 1:5 to 1:15, still more preferably 1:5.5 to 110.5, and most preferably 1:6 to 1:10. If the weight ratio of the titanium oxide (b) to the activated carbon (a) is less than the range (the amount of the titanium oxide (b) is small), the titanium oxide-coated activated, carbon (A) becomes ray to black. Such a body odor suppressing agent may cause application soiling and have lower practical aptitude. If the weight ratio of the titanium oxide (b) to the activated carbon (a) is more than the range the amount of the titanium oxide (b) is large), the titanium oxide-coated activated carbon (A) may have a lower adsorption capacity to deteriorate the body odor suppressing effects of the body odor suppressing agent of the present invention.

The total amount of the activated carbon (a) and the titanium oxide (b) in the titanium oxide-coated activated carbon (A) is not particularly limited, but is preferably 50% by weight or more (50 to 100% by weight), more preferably 70% by weight or more, and even more preferably 80% by weight or more relative to 100% by weight of the titanium oxide-coated activated, carbon (A). The upper limit is not particularly limited and is preferably 100% by weight or less and more preferably 99.95% by weight or less. The upper limit may be 90% by weight or less or 85% by weight or less.

The amount of the resins in the titanium oxide-coated activated carbon (A) is not particularly limited, but is preferably 0.005 to 10% by weight and more preferably 0.05 to 1% by weight relative to 100% by weight of the titanium oxide-coated activated carbon (A) in terms of improving the adhesiveness of the titanium oxide (b) to the activated carbon (a).

In the titanium oxide-coated activated carbon (A), the titanium oxide (b) is present over the surface of the activated carbon (a). In other words, the titanium oxide-coated activated carbon (A) has the configuration in which the activated carbon (a) is coated with the titanium oxide (b). In the titanium oxide-coated activated, carbon (A), the entire surface of the activated carbon (a) may be coated with the titanium oxide (b), or only a part of the surface of the activated carbon (a) may be coated with the titanium oxide (b).

The titanium oxide-coated activated carbon (A) is formed by attaching the titanium oxide (b) to the surface of the activated carbon (a). The titanium oxide-coated activated carbon (A) is preferably formed by attaching the titanium oxide (b) to the surface of the activated carbon (a) through the resin.

The titanium oxide-coated activated carbon. (A) can be produced by any known method, which is exemplified by the method for producing a white activated carbon disclosed in JP-A No. 4-256436 and the method for producing a titanium oxide-coated activated carbon disclosed in JP-A No. 2005-263610.

The method for producing the titanium oxide-coated activated carbon (A) is specifically exemplified as follows: The activated carbon (a), the titanium oxide (b), and an emulsion of the resins are mixed, thus coating the surface of the activated carbon (a) with the titanium oxide (b). Next, the obtained activated carbon (a) coated with the titanium oxide (b) is dried and, as necessary, crushed into granules, thereby yielding the titanium oxide-coated activated carbon (A).

The amount of the titanium oxide-coated activated carbon (A) in the body odor suppressing agent of the present invention is not particularly limited, but is preferably 0.0001 to 70% by weight and more preferably 0.001 to 30% by weight relative to 100% by weight of the body odor suppressing agent of the present invention. If containing the titanium oxide-coated activated carbon (A) in an amount of less than 0.0001% by weight, the body odor suppressing agent may have insufficient body odor suppressing effects. If containing the titanium oxide-coated activated carbon (A) in an amount of more than 70% by weight, the body odor suppressing agent may cause white residues on the skin.

The body odor suppressing agent of the present invention, may contain other components in addition to the titanium oxide-coated activated carbon (A). Each component contained in the body odor suppressing agent of the present invention may be one type or two or more types.

The body odor suppressing agent of the present invention may contain antiperspirant components. The antiperspirant component is a drug that constricts the skin to prevent sweat from generating. Examples of the antiperspirant component include, but are not necessarily limited to, aluminum chloride, aluminum potassium sulfate, aluminum sulfate, aluminum acetate, chlorohydroxy aluminum, allantoin chlorohydroxy aluminum, and zinc p-phenolsulfonate.

The body odor suppressing agent of the present invention may contain bactericidal components. The bactericidal component is a drug suppressing the proliferation of skin normal florae that generate substances causing body odor. Examples of the bactericidal component include, but are not necessarily limited to, benzalkonium chloride, benzethonium chloride, chlorhexidine hydrochloride, phenol, trichlorocarbanilide, chlorhexidine gluconate, isopropylmethylphenol, triclosan, salicylic acid, sorbic acid, and lysozyme chloride.

The body odor suppressing agent of the present invention may contain other deodorant components in addition to the titanium oxide-coated activated carbon (A). The deodorant component is a drug having the effect of removing odors, that reacts with substances generating odors, adsorbs substances generating odors, or masks odors. Examples of the deodorant component include, but are not necessarily limited to, metal oxides such as zinc oxide, silica, alkyl diethanolamide, hydroxyapatite, tea extracts, perfume, and antioxidants.

The body odor suppressing agent of the present invention may appropriately contain oils and fats, waxes, hydrocarbon oils, ester oils, silicone oils, algefacients, lower alcohols, higher alcohols, polyhydric alcohols, thickeners, antioxidants, sequestrants, animal extracts, plant extracts, pH adjusters, moisturizers, surfactants, antiseptics, powders, pharmaceutical drugs such as vitamins, colorants, propellants, and water, for example.

Examples of the oil and fat include, but are not necessarily limited to, avocado oil, camellia oil, macadamia nut oil, olive oil, and castor oil. Examples of the waxes include, but are not necessarily limited to, carnauba wax, candelilla wax, jojoba oil, beeswax, and lanolin. Examples of the hydrocarbon oil include, but are not necessarily limited to, liquid paraffin, paraffin, vaseline, ceresin, microcrystalline wax, squalene, and squalane. Examples of the ester oil include, but are not necessarily limited to, isopropyl palmitate, isopropyl myristate, propylene glycol monostearate, propylene glycol monolaurate, and polyglyceryl isostearate. Examples of the silica oil include, but are not necessarily limited to, chain silicones such as methylpolysiloxane, highly polymerized methylpolysiloxanes having a mean degree of polymerization of 650 to 7,000, methylphenylpolysiloxane, and methylhydrogenpolysiloxane; cyclic silicones such as methylcyclopolysiloxane, octamethylcyclotetrasiloxane, decamethylcyclopentasiloxane, and dodecamethylcyclohexasiloxane; amino-modified silicones such as aminopropylmethylsiloxane/dimethylsiloxane copolymers, aminoethylaminopropylsiloxane/dimethylsiloxane copolymers, and aminoethylaminopropylmethylsiloxane/dimethylsiloxane copolymers; and modified silicones such as carboxy-modified silicones, fatty acid-modified silicones, alcohol-modified silicones, aliphatic alcohol-modified silicones, epoxy-modified silicones, fluorine-modified silicones, and alkyl-modified silicones.

Examples of the lower alcohol include, but are not necessarily limited to, ethanol and isopropyl alcohol. Examples of the higher alcohol include, but are not necessarily limited to, lauryl alcohol and stearyl alcohol. Examples of the polyhydric alcohol include, but are not necessarily limited to, glycerin, diglycerin, dipropylene glycol, 1,3-butanediol, 1,2-pentanediol, 1,2-hexanediol, 1,2-octanediol, and 1,2-decanediol.

Examples of the surfactant include, but are not necessarily limited to, nonionic surfactants such as alkyl glyceryl ethers, polyoxyalkylene alkyl ethers, polyoxyalkylene hydrogenated castor oils, glycol fatty acid esters, glyceryl fatty acid esters, polyoxyalkylene glyceryl ether fatty acid esters, sorbitan fatty acid esters, polyoxyalkylene sorbitan fatty acid esters, and silicone surfactants; anionic surfactants such as alkylsulfate salts, polyoxyethylene alkyl ether sulfate, acyl-N-methyltaurine salts, alkyl ether phosphate salts, and N-acylamino acid salts; cationic surfactants such as alkyltrimethylammonium chloride and dialkyldimethylammonium chloride; and amphoteric surfactants such as betaine alkyldimethylaminoacetates and betaine alkylamidopropyldimethylaminoacetates.

Examples of the algefacient include, but are not necessarily limited to, menthol, menthyl glyceryl ether, menthyl lactate, mentha oil (HAKKAYU), peppermint oil, camphor, and icilin. Examples of the thickener include, but are not necessarily limited to, bentonite, carrageenan, carboxyvinyl polymers, and hydroxymethylcellulose. Examples of the antioxidant include, but are not necessarily limited to, tocopherol and derivatives thereof and ascorbic acid and derivatives thereof. Examples of the sequestrant include, but are not necessarily limited to, edetates, phosphoric acid, and sodium polyphosphate. Examples of the pH adjuster include, but are not necessarily limited to, citric acid and tartaric acid.

Examples of the powder include, but are not necessarily limited to, inorganic powders such as talc, kaolin, sericite, mica, silicic anhydride, magnesium aluminum silicate, zeolite, and apatite; organic powders such as cellulose powder, silk powder, and corn starch; and synthetic polymer powders such as polyethylene powder, nylon powder, polyalkyl acrylate, cross-linked polystyrene, methylsiloxane network polymers, cross-linked silicone/network silicone block copolymers, and silicone elastomers.

If the body odor suppressing agent of the present invention is specifically an aerosol spray, propellants are preferably contained. The propellant may be any propellant commonly used for cosmetics, and is exemplified by liquefied petroleum gas.

The body odor suppressing agent of the present invention may be prepared into various forms such as lotions, aerosol sprays, natural sprays, sticks, powders, roll-ons, creams, gels, emulsions, sheets (paper), body soaps (such as body shampoo and bar soap), and cosmetics for washing hair (such as shampoo and rinse), Specifically, the form of the body odor suppressing agent of the present invention is preferably aerosol sprays, lotions, sticks, roll-ons, creams, and wiper sheets and more preferably aerosol sprays. The body odor suppressing agent of the present invention may be prepared into dosage forms by a commonly known preparation method.

The body odor suppressing agent of the present invention is a deodorizer (also called deodorant) used for suppressing body odor. The body odor suppressing agent of the present invention is preferably, for example, a body odor suppressing agent for skin, used for the skin, a body odor suppressing agent for clothes, used for clothes, or a body odor suppressing agent for footwear, used for footwear, in terms of having effects of preventing application soiling. The body odor suppressing agent is particularly preferably body odor suppressing agents that are applied (especially, directly applied) to the skin, clothes, or footwear. The application (direct application) also includes application by spraying or jetting. If prepared into a standing or hanging deodorizer, the agent may insufficiently achieve the advantageous effects of the present invention. Examples of the body area to which the body odor suppressing agent of the present invention is applied include, but are not necessarily limited to, the axilla, the arms, the legs, the soles, the neck, the chest, and the buttocks. Examples of the clothes include, but are not necessarily limited to, jackets, shirts, coats, T-shirts, sweatshirts, sweaters, sweatpants, trousers, slacks, jeans, skirts, one-piece dresses, dresses, underwear, pajamas, yukatas (Japanese summer kimonos), headwear, scarfs, bandannas, mufflers, neckties, gloves, obis, belts, socks, tabi socks, leg warmers, and tights. Examples of the footwear include, but are not necessarily limited to, shoes, sneakers, high-heeled shoes, pumps, mules, boots, sandals, slippers, and getas (Japanese clogs).

The body odor suppressing agent of the present invention used as an aerosol spray will be described in further detail hereinafter. The body odor suppressing agent of the present invention used as the aerosol spray is composed exclusively of a stock solution at least containing the titanium oxide-coated activated carbon (A) and a propellant.

In the present specification, all components except propellants in the aerosol spray are called "stock solution". In other words, in 100% by weight of the body odor suppressing agent of the present invention used as the aerosol spray, the total amount of the stock solution and the propellant is 100% by weight. The amount of the stock solution is not particularly limited, but is preferably 1 to 80% by weight and more preferably 5 to 70% by weight relative to 100% by weight of the body odor suppressing agent of the present invention.

The stock solution contains the titanium oxide-coated activated carbon (A) as an essential component The amount of the titanium oxide-coated activated carbon (A) in the stock solution is not particularly limited, but is preferably 0.01 to 80% by weight and more preferably 0.1 to 60% by weight relative to 100% by weight of the stock solution. If the amount of the titanium oxide-coated activated carbon (A) is less than 0.01% by weight, such a body odor suppressing agent may achieve insufficient body odor suppressing effects. If the amount of the titanium oxide-coated activated carbon (A) is more than 80% by weight, such a body odor suppressing agent may generate white residues.

The stock solution preferably contains ester oils and specifically preferably contains isopropyl myristate. The amount of the ester oil (specifically isopropyl myristate) in the stock solution is not particularly limited, but is preferably 10 to 90% by weight and more preferably 30 to 80% by weight relative to 100% by weight of the stock solution in terms of the compatibility between gas and the stock solution.

The body odor suppressing agent of the present invention used as the aerosol spray can be produced by a known method for producing an aerosol spray. The method is not particularly limited, but is exemplified by a method of placing the stock solution into a container for aerosol, clinching the container with a valve for aerosol, then packing a predetermined amount of a propellant through a stem, and installing a button suited for the stem.

When the body odor suppressing agent of the present invention is used as a lotion, the amount of the titanium oxide-coated activated carbon (A) in the body odor suppressing agent is not particularly limited, but is preferably 0.0001 to 50% by weight and more preferably 0.01 to 10% by weight relative to 100% by weight of the body odor suppressing agent. If containing the titanium oxide-coated activated carbon (A) in an amount of less than 0.0001% by weight, the body odor suppressing agent may achieve insufficient body odor suppressing effects. If containing the titanium oxide-coated activated carbon (A) in an amount of more than 50% by weight, the body odor suppressing agent may have a lower feeling of use. The body odor suppressing agent of the present invention used as the lotion can be produced by a known method for producing a lotion.

When the body odor suppressing agent of the present invention is used as a stick, the amount of the titanium oxide-coated activated carbon (A) in the body odor suppressing agent is not particularly limited, but is preferably 0.0001 to 50% by weight and more preferably 0.01 to 30% by weight relative to 100% by weight of the body odor suppressing agent. If containing the titanium oxide-coated activated carbon (A) in an amount of less than 0.0001% by weight, the body odor suppressing agent may achieve insufficient body odor suppressing effects. If containing the titanium oxide-coated activated carbon (A) in an amount of more than 50% by weight, the body odor suppressing agent may have a lower feeling of use. The body odor suppressing agent of the present invention used as the stick can be produced by a known method for producing a stick.

When the body odor suppressing agent of the present invention is used as a roll-on, the amount of the titanium oxide-coated activated carbon (A) in the body odor suppressing agent is not particularly limited, but is preferably 0.0001 to 50% by weight and more preferably 0.01 to 30% by weight relative to 100% by weight of the body odor suppressing agent. If containing the titanium oxide-coated activated carbon (A) in an amount of less than 0.0001% by weight, the body odor suppressing agent may achieve insufficient body odor suppressing effects. If containing the titanium oxide-coated activated carbon (A) in an amount of more than 50% by weight, the body odor suppressing agent may have a lower feeling of use. The body odor suppressing agent of the present invention used as the roll-on can be produced by a known method for producing a roll-on.

When the body odor suppressing agent of the present invention is used as a cream, the amount of the titanium oxide-coated activated carbon (A) in the body odor suppressing agent is not particularly limited, but is preferably 0.0001 to 50% by weight and more preferably 0.01 to 30% by weight relative to 100% by weight of the body odor suppressing agent. If containing the titanium oxide-coated activated carbon (A) in an amount of less than 0.0001% by weight, the body odor suppressing agent may achieve insufficient body odor suppressing effects. If containing the titanium oxide-coated activated carbon (A) in an amount of more than 50% by weight, the body odor suppressing agent may have a lower feeling of use. The body odor suppressing agent of the present invention used as the cream can be produced by a known method for producing a cream.

The body odor suppressing agent of the present invention used as a sheet (for example, wiper sheet) will be described in further detail hereinafter. The body odor suppressing agent of the present invention used as the sheet includes a sheet-like base material and a stock solution that at least contains the titanium oxide-coated activated carbon (A) and is infiltrated into the sheet-like base material. The amount of the titanium oxide-coated activated carbon (A) in the stock solution is not particularly limited, but is preferably 0.0001 to 50% by weight and more preferably 0.01 to 30% by weight relative to 100% by weight of the stock solution. If the amount of the titanium oxide-coated activated carbon (A) is less than 0.0001% by weight, such a body odor suppressing agent may achieve insufficient body odor suppressing effects. If the amount of the titanium oxide-coated activated, carbon (A) is more than 50% by weight, such a body odor suppressing agent may have a lower feeling of use. The body odor suppressing agent of the present invention used as the sheet (for example, wiper sheet) can be produced by a known method for producing a sheet.

The titanium oxide-coated activated carbon (A) in the body odor suppressing agent of the present invention has markedly higher body odor suppressing effects than those of deodorant components used in conventional body odor suppressing agents. If further containing antiperspirants or antiseptics, the body odor suppressing agent of the present invention can have higher body odor suppressing effects. On this account, the body odor suppressing agent of the present invention can exert excellent body odor suppressing effects that cannot be achieved by conventional body odor suppressing agents.

In addition, the titanium oxide-coated activated carbon (A) is white. The body odor suppressing agent of the present invention thus causes no black soiling on an object when applied to the object. On this account, the body odor suppressing agent can be applied to the skin, clothes, or footwear, and has excellent practical aptitude. A body odor suppressing agent containing a black activated carbon in place of the titanium oxide-coated activated carbon (A) causes black soiling on an object to be coated, such as the skin and clothes, and thus cannot be directly applied to such an object in practice.

The titanium oxide-coated activated carbon (A) has a small average particle diameter. The agent thus causes no roughness on the skin after coating when applied to the skin, and has an excellent feeling of use. When packed into a spray container to be used as a spray, specifically as an aerosol spray, the agent can prevent the nozzle (spray port) of the spray container from clogging. On this account, the body odor suppressing agent of the present invention is also useful as the aerosol spray.

EXAMPLES

The present invention will now be described in further detail with reference to examples, but is not limited to these examples. The amounts are expressed in terms of "% by weight" unless otherwise specified.

Production Example of Titanium Oxide-Coated Activated Carbon (A-1)

Activated carbon (trade name "GW-B32/60", manufactured by Kuraray Chemical Co., Ltd.) was crushed with a crusher and then classified, giving an activated carbon (powdered activated carbon) having an average particle diameter of 40.9 μm.

Next, 1.8 g of the activated carbon (an average particle diameter of 40.9 μm) obtained above was mixed with 10.8 g of a titanium oxide (trade name "CR-50", manufactured by ISHIHARA, SANGYO KAISHA, LTD., an average particle diameter of 0.25 μm), giving a mixture (1).

Separately, to 0.1 g of 45% alkyl acrylate copolymer solution (trade name "YODOSOL GH800F", manufactured by AkzoNobel), 0.02 g of 3% aqueous carboxymethylcellulose (CMC) solution and 2.5 g of purified water were added, and the whole was thoroughly stirred, giving a mixed solution (2).

While the mixed solution (2) was stirred, the mixture (1) was mixed with the mixed solution (2), giving a mixed solution (3). Next, the obtained mixed solution (3) was dried at 115° C. for 2 hours, and the dried product was crushed into powder with a crusher, giving a titanium oxide-coated activated carbon (A-1).

Production Example of Titanium Oxide-Coated Activated Carbons (A-2) to (A-10), (B-1), and (B-2)

Titanium oxide-coated activated carbons (A-2), (A-3), (A-4), (A-5), (A-6), (A-7), (A-8), (A-9), (A-10), (B-1), and (B-2) were obtained in the same manner as in the "Production Example of Titanium Oxide-Coated Activated Carbon (A-1)" except that the average particle diameter and the raw material of the activated carbon, the average particle diameter of the titanium oxide, the mixing ratio of the activated carbon and the titanium oxide, and other conditions were changed as shown in Table 1.

Production Example of Activated Carbon (C-1)

The activated carbon (covered with no titanium oxide) having an average particle diameter of 40.9 μm produced in the "Production Example of Titanium Oxide-Coated Activated Carbon (A-1)" was regarded as an activated carbon (C-1).

(Evaluation)

Each of (A-1) to (A-10), (B-1), (B-2), and (C-1) obtained in the Production Examples was evaluated in the following manner, The evaluation results are shown in Table 1. Hereinafter, (A-1) to (A-10), (B-1), (B-2), and (C-1) are also called "each powder obtained in Production Examples".

(1) Lightness (L*Value)

Each powder obtained in Production Examples was filled into to plastic container having a bottom radius of 1.0 cm and a depth of 0.6 cm, giving a sample. Next, with a spectrophotometer (trade name "SPECTROPHOTOMETER CM-2600d", manufactured by KONICA MINOLTA, INC.), the lightness (L*value) of each sample was determined, and the soiling preventive effect was evaluated in accordance with the following evaluation criteria.

<Evaluation Criteria>

A (excellent): the L*value is 80 or more and 100 or less (white).

B (good): the L*value is 75 or more and less than 80 (white to grayish white).

C (usable): the L*value is 70 or more and less than 75 (grayish white to gray).

D (poor): the L*value is less than 70 (gray to black).

The L*value is a value expressed by the L*a*b* color system and is also defined in JIS Z 8729.

(2) Capacity of Adsorbing Body Odor Component (Isovaleric Acid) Generated From Human In a vial (a volume of 15 mL), 300 μL of 1.0% by volume aqueous isovaleric acid solution and 60 mg of each powder obtained in Production Examples were placed. The vial was sealed and allowed to stand at 35° C. for 30 minutes. Next, from the head space of the vial, 1 mL of a sample was collected with a gas-tight syringe.

With a gas chromatograph-hydrogen flame ionization detector (GC-FID), the amount of isovaleric acid in each sample was determined under the following conditions. Specifically, the area value (peak area) of isovaleric acid was determined.

Separately, the area value of isovaleric acid without powders was determined in the same manner as the above except that no powder was added, and was regarded as a standard value (control).

The standard value (area value without powders) was compared with the area value of isovaleric acid in each sample, and the adsorption ratio (%) of each sample was calculated in accordance with the following formula.

Adsorption ratio (%)=[1−(area value of sample/standard value)]×100

<G-FID Analysis Conditions>

Column used: trade name "DB-1701" (a length of 30 m, an inner diameter of 0.25 mm, a film thickness of 1 μm) manufactured by Agilent Technologies, Inc.

Gas used: helium gas

Temperature condition: temperature rise from 40° C. to 150° C. (a rate of temperature rise of 5° C./min), temperature rise from 150° C. to 280° C. (a rate of temperature rise of 10° C./min)

Detection: hydrogen flame ionization detector (FID)

The capacity of each powder adsorbing isovaleric acid was classified in accordance with the following classification criteria.

<Classification Criteria for Adsorption Capacity>
A (excellent): the adsorption ratio is 70% or more and 100% or less.
B (good): the adsorption ratio is 50% or more and less than 70%.
C (usable): the adsorption ratio is 35% or more and less than 50%.
D (poor): the adsorption ratio is less than 35%.

Silicic anhydride (trade name "SILICA MICROBEAD P-1500" manufactured by Catalysts & Chemicals Ind. Co. Ltd.) commonly used as a deodorant component had an isovaleric acid-adorption capacity of about 35%.

(3) Feeling of Use

Ten subjects evaluated each powder obtained in Production Examples by the following test method.

<Test Method>

To the medial surface of the upper arm of the subject, 5 mg of each powder obtained in Production Examples was applied, and the feeling of use was evaluated in accordance with the following evaluation criteria. The scores of ten subjects were averaged, and the classification was carried out from the calculated average in accordance with the following classification criteria.

<Evaluation Criteria>
Score 4: the applied area is very smooth.
Score 3: the applied area is smooth.
Score 2: the applied area is slightly rough.
Score 1: the applied area is very rough.

<Classification Criteria>
A (excellent): the average score is 3.6 or higher
B (good): the average score is 3.0 or higher and lower than 3.6
C (usable): the average score is 2.0 or higher and lower than 3.0.
D (poor): the average score is less than 2.0.

(4) Application Soiling

Each body odor suppressing agent obtained in Examples and Comparative Examples was evaluated by the following test method.

<Test Method>

Each body odor suppressing agent obtained in Examples and Comparative Examples (an application amount of 500 mg) was applied to the e medial surface of the upper arm of the subject, and the application soiling preventive effect was visually evaluated in accordance with the following classification criteria.

<Classification Criteria>
B (excellent): no black soiling is observed on the applied area.
C (usable): black soiling is slightly observed on the applied area.
D (poor): black soiling is clearly observed on the applied area.

(5) Feeling of Use

Ten subjects evaluated each body odor suppressing agent obtained in Examples and Comparative Examples by the following test method.

<Test Method>

Each body odor suppressing agent obtained in Examples and Comparative Examples (an application amount of 500 mg) was applied to the medial surface of the upper arm of the subject, and the feeling of use was evaluated in accordance with the following evaluation criteria. The scores of ten subjects were averaged, and the classification was carried out from the calculated average in accordance with the following classification criteria.

<Evaluation Criteria>
Score 4: the applied area is very smooth.
Score 3: the applied area is smooth.
Score 2: the applied area is slightly rough.
Score 1: the applied area is very rough.

<Classification Criteria>
A (excellent): the average score is 3.6 or higher,
B (good): the average score is 3.0 or higher and lower than 3.6.
C (usable): the average score is 2.0 or higher and lower than 3.0.
D (poor): the average score is lower than 2.0.

TABLE 1

| | Activated carbon | | Titanium oxide | Mixing ratio of activated carbon and titanium oxide [activated carbon:titanium oxide] (weight ratio) | Lightness ($L^*$ value) | Adsorption capacity (isovaleric acid) | Feeling of use |
|---|---|---|---|---|---|---|---|
| | Average particle diameter (μm) | Raw material | Average particle diameter (μm) | | | | |
| A-1 | 40.9 | Coconut shell | 0.25 | 100:600 | A | A | A |
| A-2 | 20.0 | Coconut shell | 0.25 | 100:600 | B | A | A |
| A-3 | 40.9 | Coconut shell | 0.05-0.07 | 100:600 | A | A | A |
| A-4 | 40.9 | Coconut shell | 0.25 | 100:500 | C | A | A |
| A-5 | 40.9 | Coconut shell | 0.25 | 100:700 | A | A | A |
| A-6 | 40.9 | Coconut shell | 0.25 | 100:800 | A | B | A |
| A-7 | 40.9 | Coconut shell | 0.25 | 100:1000 | A | B | A |
| A-8 | 40.9 | Coconut shell | 0.05-0.07 | 100:500 | C | A | A |
| A-9 | 40.9 | Coconut shell | 0.03-0.05 | 100:500 | C | A | A |
| A-10 | 40.9 | Coconut shell | 0.01-0.03 | 100:500 | C | A | A |
| B-1 | 9.4 | Coconut shell | 0.25 | 100:600 | D | A | A |
| B-2 | 100.0 | Coal | 0.25 | 100:600 | C | B | D |
| C-1 | 40.9 | Coconut shell | — | — | D | A | A |

Examples 1 to 10, Comparative Examples 1 to 3

The components were mixed in accordance with the formula shown in Table 2, giving each body odor suppressing agent of Examples and Comparative Examples.

(Evaluation)

Each body odor suppressing agent obtained in Examples and Comparative Examples was evaluated in the following manner. The evaluation results are shown in Table 2.

TABLE 2

| | | Example 1 | Example 2 | Example 3 | Example 4 | Example 5 | Example 6 | Example 7 | Example 8 | Example 9 | Example 10 | Comparative Example 1 | Comparative Example 2 | Comparative Example 3 |
|---|---|---|---|---|---|---|---|---|---|---|---|---|---|---|
| Formula (% by weight) | Titanium oxide-coated activated carbon (A-1) | 1.0 | — | — | — | — | — | — | — | — | — | — | — | — |
| | Titanium oxide-coated activated carbon (A-2) | — | 1.0 | — | — | — | — | — | — | — | — | — | — | — |
| | Titanium oxide-coated activated carbon (A-3) | — | — | 1.0 | — | — | — | — | — | — | — | — | — | — |
| | Titanium oxide-coated activated carbon (A-4) | — | — | — | 1.0 | — | — | — | — | — | — | — | — | — |
| | Titanium oxide-coated activated carbon (A-5) | — | — | — | — | 1.0 | — | — | — | — | — | — | — | — |
| | Titanium oxide-coated activated carbon (A-6) | — | — | — | — | — | 1.0 | — | — | — | — | — | — | — |
| | Titanium oxide-coated activated carbon (A-7) | — | — | — | — | — | — | 1.0 | — | — | — | — | — | — |
| | Titanium oxide-coated activated carbon (A-8) | — | — | — | — | — | — | — | 1.0 | — | — | — | — | — |
| | Titanium oxide-coated activated carbon (A-9) | — | — | — | — | — | — | — | — | 1.0 | — | — | — | — |
| | Titanium oxide-coated activated carbon (A-10) | — | — | — | — | — | — | — | — | — | 1.0 | — | — | — |
| | Titanium oxide-coated activated carbon (B-1) | — | — | — | — | — | — | — | — | — | — | 1.0 | — | — |
| | Titanium oxide-coated activated carbon (B-2) | — | — | — | — | — | — | — | — | — | — | — | 1.0 | — |
| | Activated carbon (without coating) (C-1) | — | — | — | — | — | — | — | — | — | — | — | — | 1.0 |
| | Ethanol | 5.0 | 5.0 | 5.0 | 5.0 | 5.0 | 5.0 | 5.0 | 5.0 | 5.0 | 5.0 | 5.0 | 5.0 | 5.0 |
| | Dipropylene glycol | 1.0 | 1.0 | 1.0 | 1.0 | 1.0 | 1.0 | 1.0 | 1.0 | 1.0 | 1.0 | 1.0 | 1.0 | 1.0 |
| | Water | 93.0 | 93.0 | 93.0 | 93.0 | 93.0 | 93.0 | 93.0 | 93.0 | 93.0 | 93.0 | 93.0 | 93.0 | 93.0 |
| | Total | 100.0 | 100.0 | 100.0 | 100.0 | 100.0 | 100.0 | 100.0 | 100.0 | 100.0 | 100.0 | 100.0 | 100.0 | 100.0 |
| Evaluation result | Application soiling | B | B | B | B | B | B | B | B | B | B | D | C | D |
| | Feeling of use | A | A | A | A | A | A | A | A | A | A | A | D | A |

As apparent from the results shown in Table 2, the body odor suppressing agents (Examples 1 to 10) of the present invention were excellent body odor suppressing agents having an excellent feeling of use and preventing the application soiling when used.

In contrast, the agent (Comparative Example 2) including the titanium oxide-coated activated carbon having an average particle diameter of more than 50 μm in place of the titanium oxide-coated activated carbon (A) gave a rough feeling and had a lower feeling of use when used.

The agent (Comparative Example 1) including the titanium oxide-coated activated carbon containing the activated carbon having an average particle diameter of less than 15 μm in place of the titanium oxide-coated activated carbon (A) and the agent (Comparative Example 3) including the activated carbon coated with no titanium oxide gave black soiling on the application area when used.

(Evaluation)

The body odor suppressing effects of each body odor suppressing agent obtained in Example 1 and Example 7 were also evaluated in the following manner.

(6) Body Odor Suppressing Effects

Ten subjects evaluated each body odor suppressing agent obtained in Example 1 and Example 7 by the following test method.

<Test Method>

The axillae of the subject was cleaned with unscented soap, and then each body odor suppressing agent (an application amount of 2.0 g) was applied to one of the axillae (applied area). For comparison, no body odor suppressing agent was applied to the other of the axillae (unapplied area), At 8 hours after the application, three specialists evaluated odors of both the axillae (applied area, unapplied area) in accordance with the following evaluation criteria. The scores of ten subjects were averaged, and the calculated average was regarded as the evaluation result (grade).

<Evaluation Criteria for Odor Strength>

Score 0: no odor
Score 1: a slight odor
Score 2: a weak odor
Score 3: an obvious odor
Score 4: a slightly strong odor
Score 5: a very strong odor As a result of the evaluation of body odor suppressing effects in (6), the body odor suppressing agent obtained in Example 1 had a grade of 2.2 in the applied area and a grade of 3.2 in the unapplied area. The body odor suppressing agent obtained in Example 7 had a grade of 2.4 in the applied area and a grade of 3.2 in the unapplied area.

As described above, the body odor suppressing agents (Examples 1 and 7) of the present invention had excellent body odor suppressing effects.

Example 11 (Aerosol Spray)

A composition composed of the following components was packed into an aerosol container through a stem, and a button suited for the stem was installed, yielding an aerosol spray (deodorant spray). The stem had a pore size of 0.51 mm, and a housing had a lower pore size of 1.58 mm and a lateral pore size of 0.76 mm.

(Formula for Aerosol Spray)

| Titanium oxide-coated activated carbon (A-1) | 2.0% by weight |
| Isopropyl myristate | 2.0% by weight |
| Methylphenylpolysiloxane | 0.02% by weight |
| LPG | 95.98% by weight |

(7) Evaluation of Aerosol Spray

The aerosol spray obtained in Example 11 was shook well for 5 seconds and then sprayed for 3 seconds. The operation was continuously repeated. The composition caused no clogging and was able to be completely sprayed. In other words, the body odor suppressing agent of the present invention had excellent characteristics of capable of preventing nozzles from clogging when used as the spray.

Production Example of Titanium Oxide-Coated Activated Carbon (A-11)

Activated carbon (trade name "GW-B32/60", manufactured by Kuraray Chemical Co., Ltd.) was crushed with a crusher and then classified, giving an activated carbon (powdered activated carbon) having an average particle diameter of 40.9 μm.

Separately, to 0.1 g of 45% alkyl acrylate copolymer solution (trade name "YODOSOL GH800F", manufactured by AkzoNobel), 5.1 g of purified water was added, and the whole was thoroughly stirred, giving a mixed solution (4).

While the mixed solution (4) was stirred, the mixture (4) was mixed with 1.8 g of the activated carbon obtained above (an average particle diameter of 40.9 μm), giving a mixed solution (5).

To the obtained mixed solution (5), 10.8 g of a titanium oxide (trade name "CR-50", manufactured by ISHIHARA SANGYO KAISHA, LTD., an average particle diameter of 0.25 μm) was mixed, giving a mixture (6).

Next, the obtained mixed solution (6) was dried at 115° C. for 2 hours and crushed into powder with a crusher, giving a titanium oxide-coated activated carbon (A-11).

Example 12 (Aerosol Spray)

A composition composed of the following components was packed into an aerosol container through a stem, and a button suited for the stem was installed, yielding an aerosol spray (deodorant spray). The aerosol spray also had excellent body odor suppressing effects.

(Formula for Aerosol Spray)

| Titanium oxide-coated activated carbon (A-11) | 1.5% by weight |
| isopropyl myristate | 3.5% by weight |
| LPG | 95.0% by weight |

Formulation examples of the body odor suppressing agent of the present invention will be shown below.

Formulation Example 1

Deodorant Spray (Aerosol Spray)

A stock solution composed of the following components and a propellant composed of the following component were packed into an aerosol container through a stem so as to give a weight ratio (stock solution/propellant) of 5/95, and a button suited for the stem was installed, yielding a deodorant spray.

Formula for Stock Solution

| Talc | 20.0% by weight |
| Silicic anhydride | 10.0% by weight |
| Chlorohydroxy aluminum | 10.0% by weight |
| Titanium oxide-coated activated carbon (A-1) | 10.0% by weight |
| Menthol | 1.5% by weight |
| Triclosan | 0.1% by weight |
| Dimethylpolysiloxane | 15.0% by weight |
| Perfume | appropriate amount |
| Isopropyl myristate | remainder |
| Total | 100.0% by weight |

(Formula for Propellant)

| LPG | 100.0% by weight |

Formulation Example 2

Deodorant Stick

The following raw materials were mixed so as to give the following formula, and formed into a deodorant stick in a usual manner.

| | |
|---|---|
| Isopropylmethylphenol | 0.2% by weight |
| Aluminum potassium sulfate | 20.0% by weight |
| Chlorohydroxy aluminum | 10.0% by weight |
| Stearyl alcohol | 5.0% by weight |
| Glyceryl monostearate | 3.0% by weight |
| Titanium oxide-coated activated carbon (A-1) | 10.0% by weight |
| Silicic anhydride | 25.0% by weight |
| Candelilla wax | 0.5% by weight |
| Castor oil | 0.1% by weight |
| Citral | 0.04% by weight |
| Eugenol | 0.05% by weight |
| Decamethylcyclopentasiloxane | remainder |
| Total | 100.0% by weight |

Formulation Example 3

Deodorant Gel

The following raw materials were mixed so as to give the following formula, yielding a deodorant gel.

| | |
|---|---|
| Menthol | 0.5% by weight |
| Titanium oxide-coated activated carbon (A-1) | 10.0% by weight |
| Acrylic acid/alkyl methacrylate copolymer | 0.2% by weight |
| Potassium hydroxide | 0.02% by weight |
| Isononyl isononanoate | 1.5% by weight |
| Triclosan | 0.1% by weight |
| Ethyl alcohol | 30.0% by weight |
| Perfume | appropriate amount |
| Purified water | remainder |
| Total | 100.0% by weight |

Formulation Example 4

Deodorant Roll-On

The following raw materials were mixed so as to give the following formula, yielding a deodorant roll-on.

| | |
|---|---|
| Titanium oxide-coated activated carbon (A-1) | 10.0% by weight |
| Menthol | 0.1% by weight |
| Triclosan | 0.1% by weight |
| Chlorohydroxy aluminum | 10.0% by weight |
| Isononyl isononanoate | 1.0% by weight |
| Hydroxypropylcellulose | 1.0% by weight |
| Ethyl alcohol | 60.0% by weight |
| Perfume | appropriate amount |
| Purified water | remainder |
| Total | 100.0% by weight |

Formulation Example 5

Wiper Sheet Cosmetic

Into 1 g of nonwoven fabric, 5 g of the composition composed of the following components was infiltrated, yielding a wiper sheet cosmetic.
[Formula of Composition for wiper Sheet Cosmetic]

| | |
|---|---|
| Titanium oxide-coated activated carbon (A-1) | 10.0% by weight |
| Menthol | 0.1% by weight |
| Talc | 10.0% by weight |
| Polyoxyethylene polyoxypropylene 2-decyltetradecyl ether | 0.2% by weight |
| Ethyl alcohol | 40.0% by weight |
| Perfume | appropriate amount |
| Purified water | remainder |
| Total | 100.0% by weight |

Formulation Example 6

Emulsion

The following raw materials were mixed so as to give the following formula, yielding an emulsion.

| | |
|---|---|
| Titanium oxide-coated activated carbon (A-1) | 10.0% by weight |
| Liquid paraffin | 15.0% by weight |
| Beeswax | 2.0% by weight |
| Lanolin | 1.5% by weight |
| Sorbitan sesquioleate | 2.5% by weight |
| Polyoxyethylene sorbitan monooleate | 1.0% by weight |
| 1,2-Octanediol | 0.05% by weight |
| 1,3-Butylene glycol | 13.0% by weight |
| Xanthan gum | 0.5% by weight |
| Purified water | remainder |
| Total | 100.0% by weight |

Formulation Example 7

Skin Lotion

The following raw materials were mixed so as to give the following formula, yielding a skin lotion.

| | |
|---|---|
| Titanium oxide-coated activated carbon (A-1) | 10.0% by weight |
| 1,3-Butylene glycol | 6.0% by weight |
| Glycerin | 4.0% by weight |
| Hydrolyzed hyaluronic acid | 0.1% by weight |
| Polyoxyethylene polyoxypropylene 2-decyhetradecyl ether | 0.2% by weight |
| Ethylene glycol phenyl ether | 0.3% by weight |
| Perfume | appropriate amount |
| Ethyl alcohol | 3.0% by weight |
| Purified water | remainder |
| Total | 100.0% by weight |

Formulation Example 8

Skin Care Gel

The following raw materials were mixed so as to give the following formula, yielding a skin care gel.

| | |
|---|---|
| Titanium oxide-coated activated carbon (A-1) | 10.0% by weight |
| 1,3-Butylene glycol | 10.0% by weight |
| Glycerin | 3.0% by weight |
| Dipropylene glycol | 5.0% by weight |
| Acrylic acid/alkyl methacrylate copolymer | 0.4% by weight |
| Xanthan gum | 0.01% by weight |
| Potassium hydroxide | 0.15% by weight |
| Decamethylpolysiloxane | 5.0% by weight |

-continued

| | |
|---|---|
| Trimethylglycine | 10.0% by weight |
| 1,2-Pentanediol | 0.1% by weight |
| Glycerin mono-2-ethylhexyl ether | 0.05% by weight |
| Dipotassium glycyrrhizinate | 0.1% by weight |
| Ethyl alcohol | 3.0% by weight |
| Disodium ethylenediaminetetraacetate | appropriate amount |
| Perfume | appropriate amount |
| Purified water | remainder |
| Total | 100.0% by weight |

Formulation Example 9

Skin Care Cream

The following raw materials were mixed so as to give the following formula, yielding a skin care cream.

| | |
|---|---|
| Liquid paraffin | 5.0% by weight |
| Paraffin | 5.0% by weight |
| Hydrogenated palm oil | 3.0% by weight |
| Behenyl alcohol | 3.0% by weight |
| Stearic acid | 1.0% by weight |
| Glyceryl tri-2-ethylhexanoate | 5.0% by weight |
| Xanthan gum | 0.05% by weight |
| Carboxyvinyl polymer | 0.4% by weight |
| Polyoxyethylene sorbitan monostearate | 1.5% by weight |
| Glyceryl stearate | 0.5% by weight |
| 1,3-Butylene glycol | 10.0% by weight |
| 1,2-Octanediol | 0.2% by weight |
| Titanium oxide-coated activated carbon (A-1) | 10.0% by weight |
| Glycerin mono-2-ethylhexyl ether | 0.35% by weight |
| Glycerin | 5.0% by weight |
| Potassium hydroxide | appropriate amount |
| Tocopherol | appropriate amount |
| Disodium ethylenediaminetetraacetate | appropriate amount |
| Perfume | appropriate amount |
| Purified water | remainder |
| Total | 100.0% by weight |

Formulation Example 10

Body Lotion

The following raw materials were mixed so as to give the following formula, yielding a body lotion.

| | |
|---|---|
| Titanium oxide-coated activated carbon (A-1) | 10.0% by weight |
| Menthol | 0.5% by weight |
| 1,3-Butylene glycol | 5.0% by weight |
| Nylon powder | 5.0% by weight |
| Ethyl alcohol | 50.0% by weight |
| Perfume | appropriate amount |
| Purified water | remainder |
| Total | 100.0% by weight |

Formulation Example 11

Hair Tonic

The following raw materials were mixed so as to give the following formula, yielding a hair tonic.

| | |
|---|---|
| Titanium oxide-coated activated carbon (A-1) | 10.0% by weight |
| Menthol | 0.5% by weight |
| D-Pantothenyl alcohol | 0.2% by weight |
| Nicotinic acid amide | 0.1% by weight |
| dl-α-Tocopherol acetate | 0.1% by weight |
| Camphor | 0.001% by weight |
| Polyoxyethylene hydrogenated castor oil (50 E.O.) | 0.3% by weight |
| Sodium lactate | 0.5% by weight |
| Citric acid | 0.05% by weight |
| Ethyl alcohol | 50.0% by weight |
| Perfume | appropriate amount |
| Purified water | remainder |
| Total | 100.0% by weight |

Formulation Example 12

Facial Cleanser

The following raw materials were mixed so as to give the following formula, yielding a facial cleanser.

| | |
|---|---|
| 30% by weight Betaine lauryldimethylaminoacetate liquid | 3.0% by weight |
| Laurie acid | 5.0% by weight |
| Myristic acid | 6.0% by weight |
| Palmitic acid | 4.0% by weight |
| Stearic acid | 9.0% by weight |
| Polyethylene glycol distearate (150 E.O.) | 5.0% by weight |
| 10% by weight Vinylpyrrolidone/dimethylaminopropyl methacrylamide/lauryldimethylaminopropylmethacrylamide chloride copolymer liquid | 10.0% by weight |
| Polyethylene glycol | 20.0% by weight |
| Propylene glycol | 3.0% by weight |
| Glycerin | 5.0% by weight |
| 1,2-Octanediol | 0.5% by weight |
| Hydroxypropylmethylcellulose | 0.5% by weight |
| Potassium hydroxide | 5.0% by weight |
| Titanium oxide-coated activated carbon (A-1) | 10.0% by weight |
| Ethylenediaminetetraacetate | appropriate amount |
| Perfume | appropriate amount |
| Purified water | remainder |
| Total | 100.0% by weight |

Formulation Example 13

Body Shampoo

The following raw materials were mixed so as to give the following formula, yielding a body shampoo.

| | |
|---|---|
| Lauric acid | 5.0% by weight |
| Myristic acid | 7.0% by weight |
| Propylene glycol | 4.0% by weight |
| Betaine lauryldimethylaminoacetate | 3.5% by weight |
| Potassium hydroxide | 3.6% by weight |
| Sodium sulfite | 0.03% by weight |
| Methyl p-hydroxybenzoate | 0.3% by weight |
| Ethylene glycol phenyl ether | 0.8% by weight |

-continued

| | |
|---|---|
| Titanium oxide-coated activated carbon (A-1) | 10.0% by weight |
| Ethylenediaminetetraacetate | appropriate amount |
| Perfume | appropriate amount |
| Purified water | remainder |
| Total | 100.0% by weight |

Formulation Example 14

Shampoo

The following raw materials were mixed so as to give the following formula, yielding a shampoo.

| | |
|---|---|
| Sodium polyoxyethylene lauryl ether sulfate | 6.0% by weight |
| Betaine lauryldimethylaminoacetate | 2.0% by weight |
| Sodium polyoxyethylene lauryl ether acetate | 3.0% by weight |
| Disodium lauryl sulfosuccinate | 1.0% by weight |
| Coconut oil fatty acid diacetal amide | 5.0% by weight |
| O-[2-Hydroxy-3-(trimethylammonio)propyl] hydroxyethyl cellulose chloride | 0.2% by weight |
| Dipotassium glycyrrhizinate | 0.2% by weight |
| Menthol | 1.0% by weight |
| Titanium oxide-coated activated carbon (A-1) | 10.0% by weight |
| Ethyl alcohol | 3.0% by weight |
| Sodium chloride | appropriate amount |
| Ethylenediaminetetraacetate | appropriate amount |
| Sodium benzoate | appropriate amount |
| Perfume | appropriate amount |
| Purified water | remainder |
| Total | 100.0% by weight |

Formulation Example 15

Body Powder

The following raw materials were mixed so as to give the following formula, yielding a body powder.

| | |
|---|---|
| Talc | 83.0% by weight |
| Mica | 10.0% by weight |
| Titanium oxide-coated activated carbon (A-1) | 5.0% by weight |
| Vaseline | 1.0% by weight |
| Squalane | 1.0% by weight |
| Total | 100.0% by weight |

INDUSTRIAL APPLICABILITY

The body odor suppressing agent of the present invention is preferably used as a deodorizer (also called deodorant) used for suppressing body odor. Specifically the body odor suppressing agent of the present invention is preferably used as a body odor suppressing agent for skin, used for the skin, a body odor suppressing agent for clothes, used for clothes, and a body odor suppressing agent for footwear, used for footwear.

The invention claimed is:

1. A method for suppressing body odor comprising;
a step of applying a body odor suppressing agent to skin, clothes, or footwear, the body odor suppressing agent containing a titanium oxide-coated activated carbon which includes an activated carbon having an average particle diameter of 15 to 50 μm, and
a titanium oxide present over a surface of the activated carbon, the titanium oxide having a weight ratio of 550 to 1,500 parts by weight relative to 100 parts by weight of the activated carbon.

2. The method for suppressing body odor according to claim 1, wherein the titanium oxide has an average particle diameter of 0.01 to 0.5 μm.

3. The method for suppressing body odor according to claim 1, wherein the body odor suppressing agent contains an antiperspirant component.

4. The method for suppressing body odor according to claim 1, wherein the body odor suppressing agent is applied to skin.

* * * * *